United States Patent [19]
Steyn

[11] Patent Number: 5,746,718
[45] Date of Patent: May 5, 1998

[54] NEEDLE PROTECTIVE DEVICE

[76] Inventor: Ricardo Sheath Oxford Steyn, 16 Farrow Rd., Randpark Ridge Extension 13, Randburg, Gauteng, South Africa

[21] Appl. No.: 649,533

[22] Filed: May 17, 1996

Related U.S. Application Data

[63] Continuation-in-part of Ser. No. 211,365, Jul. 5, 1994, Pat. No. 5,538,508.

[30] Foreign Application Priority Data

Jun. 19, 1995 [ZA] South Africa ............. 95/5021

[51] Int. Cl.⁶ ................................. A61M 5/00
[52] U.S. Cl. ............................ 604/192; 604/263
[58] Field of Search ................. 604/192, 110, 604/187, 198, 263; 128/919

[56] References Cited

U.S. PATENT DOCUMENTS

| | | |
|---|---|---|
| 2,674,246 | 4/1954 | Bower . |
| 4,725,267 | 2/1988 | Vaillancourt . |
| 4,955,866 | 9/1990 | Corey . |
| 4,978,344 | 12/1990 | Dombrowski et al. . |
| 4,998,922 | 3/1991 | Kuracina et al. . |
| 5,015,240 | 5/1991 | Soproni et al. . |
| 5,098,401 | 3/1992 | DeLange . |
| 5,250,031 | 10/1993 | Kaplan et al. . |
| 5,256,152 | 10/1993 | Marks . |
| 5,295,972 | 3/1994 | Mischenko . |
| 5,304,148 | 4/1994 | Lannoye et al. . |
| 5,538,508 | 7/1996 | Steyn ........................... 604/192 |

FOREIGN PATENT DOCUMENTS

| | | |
|---|---|---|
| 0 434 008 | 6/1991 | European Pat. Off. . |
| 2 243 522 | 11/1991 | United Kingdom . |
| WO89/04681 | 6/1989 | WIPO . |
| WO89/10767 | 11/1989 | WIPO . |

*Primary Examiner*—John D. Yasko
*Attorney, Agent, or Firm*—Jones, Tullar & Cooper, P.C.

[57] ABSTRACT

A needle protective device has a tubular member (14) with an end cap (16). One end (12) of the member (10) engages on needle hub (22), and the other end has a cap (16) with an opening (34). The tubular member is flexible and has cut-outs (18) in its wall. Normally the needle (26) is directed away from the opening 34) so that the needle tip is enclosed by the cap (16). To use the needle, the end cap (16) is displaced to bring the needle alongside guide ribs (38) and the tubular member (14) compressed axially to expose the needle (26) through the opening (34).

37 Claims, 3 Drawing Sheets

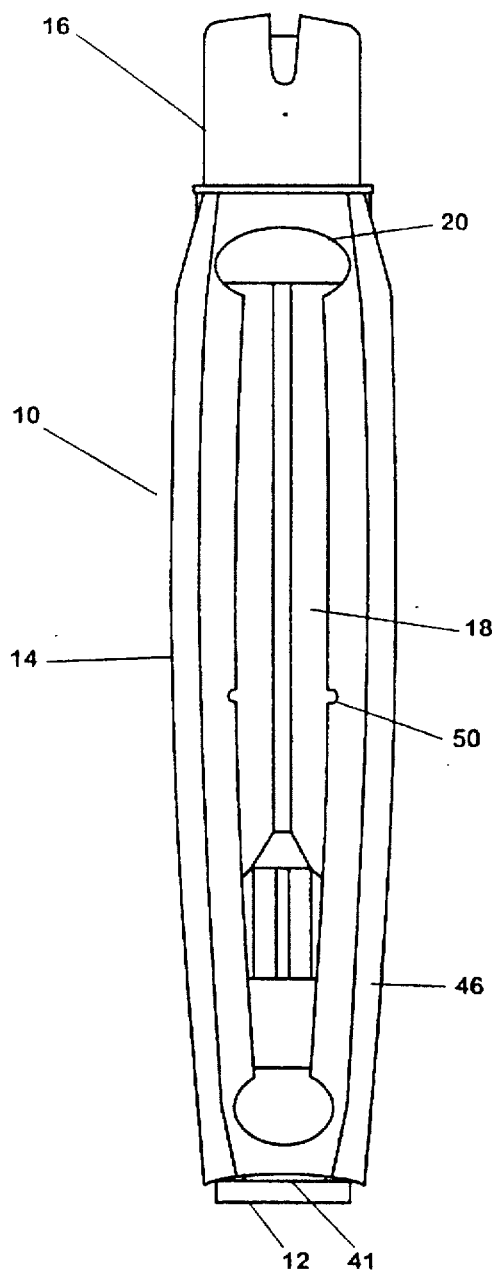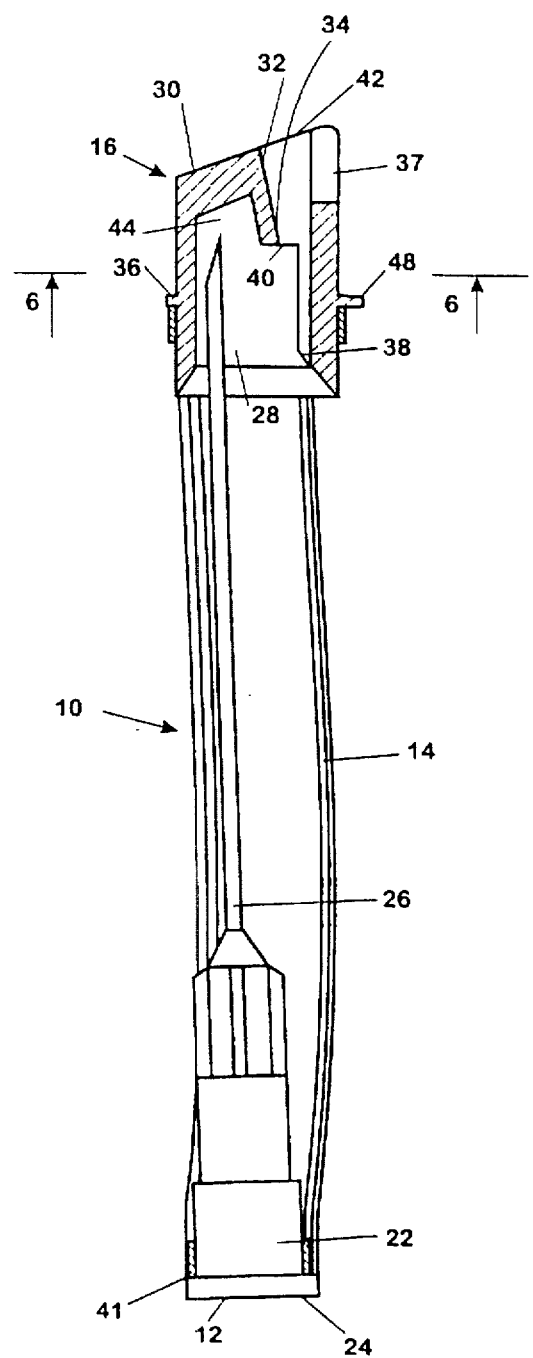
FIG. 1
FIG. 2

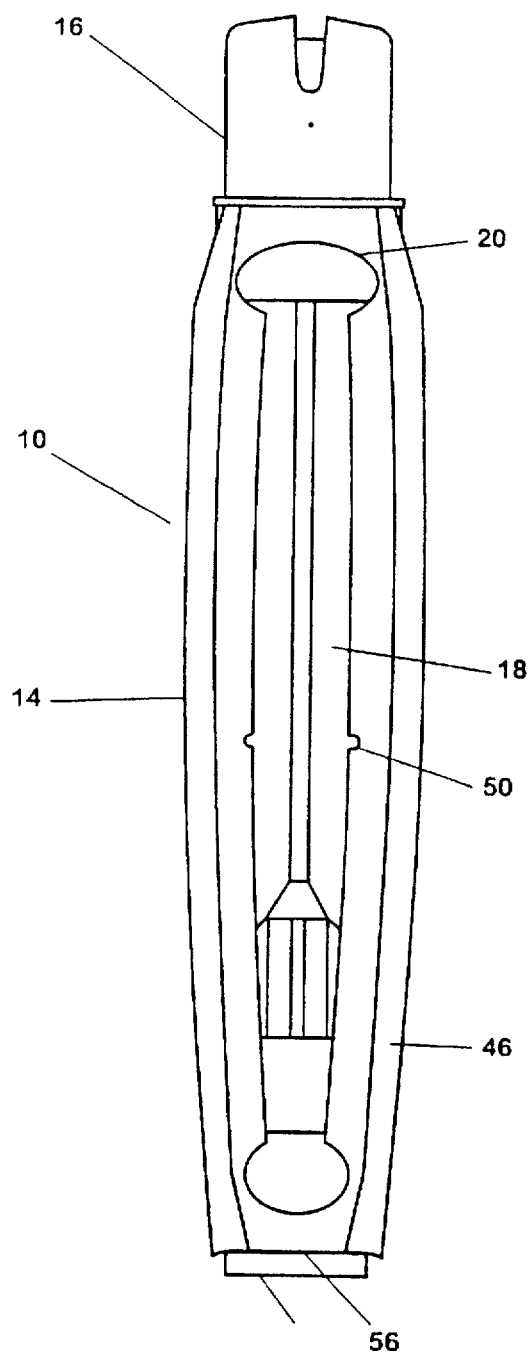
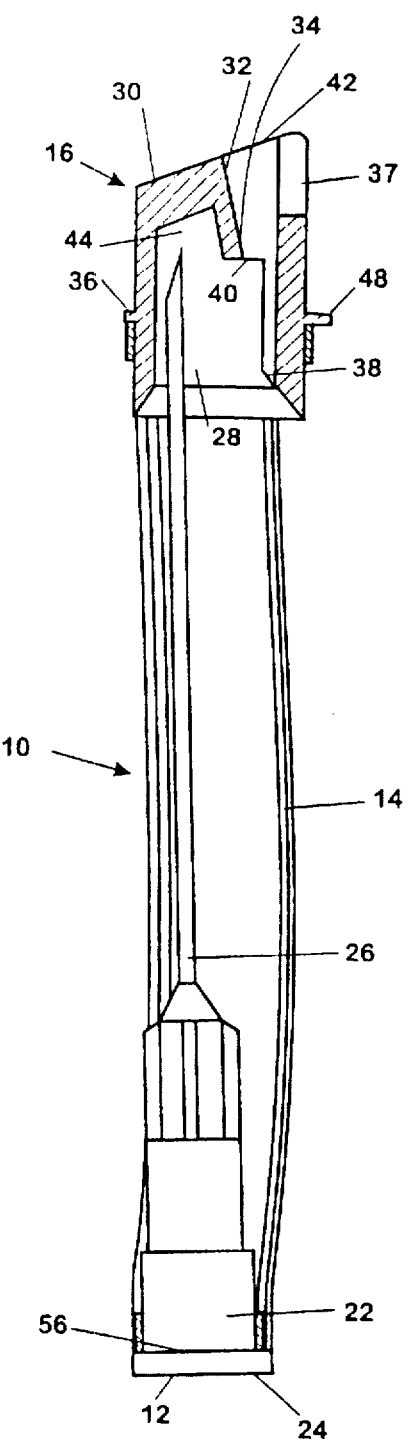
FIG. 8  FIG. 9

NEEDLE PROTECTIVE DEVICE

CROSS-REFERENCE TO RELATED APPLICATION

This application is a continuation-in-part of U.S. application Ser. No. 08/211,365 filed 5 Jul. 1994, now U.S. Pat. No. 5,538,508.

BACKGROUND TO THE INVENTION

This invention relates to a protective device for a needle of a syringe, catheter or similar medical appliance for human or animal use.

Various protective devices of this kind are known for an elongate needle of the aforementioned kind having a base at one end and a point at an opposing end which devices include a blocking surface and means which extends from the base and which supports the blocking surface, the blocking surface having a hole and being movable at least towards the base to allow the needle to extend through the hole. However these have generally suffered from the disadvantage of being relatively expensive in a field where low cost is of the greatest priority due to the large volume required.

SUMMARY OF THE INVENTION

It is an object of the present invention to provide a novel inexpensive and effective protective device of the kind described.

The invention provides a needle protective device for a needle assembly having a needle hub and a needle projecting from the hub, the needle protective device comprising, a tubular member of resilient flexible material which extends about the needle, the tubular member having first and second ends, a first end of the tubular member having a bevel thereon and being mounted skew on and frictionally engaged with the needle hub with the bevel normal to the longitudinal axis of the needle hub, and an end cap mounted on the second end of the tubular member, the end cap having a blocking surface defining a hole through which an end of the needle may pass, the skew mounting biasing the tubular member to a position in which the end of the needle opposes the blocking surface.

Preferably a plurality of cut-outs are provided in the wall of the tubular member extending in the axial direction between the first and second ends. These cut-outs which are preferably in the form of slits and diametrically opposed to each other.

According to a further preferred feature of the invention the slits terminate at either end in round holes. These holes are advantageous in that they prevent the slits from tearing.

While not essential it is preferred that at least one gripping means is provided on the exterior of the tubular member. The provision of the gripping means enables the tubular member to be gripped for stretching over the needle hub and the end cap during assembly.

The gripping means may take various forms. In one form, the gripping means consists of a flange on the tubular member at or adjacent each end. In another form the gripping means includes a plurality of formations disposed about the circumference of the tubular member. These formations may be in the form of lugs or alternatively in the form of ribs extending over at least a substantial portion of the length of the tubular member.

When the gripping means is in rib form it serves a further purpose of stiffening the tubular member.

In addition the tubular member may have protruding laterally therefrom at or adjacent each end a registration tab. This tab is used to locate and orientate the end cap in the vibrating bowls used to feed the end caps during an automated process for assembling them onto the tubular members.

The end cap may include a chamber which is open at one end which is attached to the said second end of the tubular member, the blocking surface being located at an opposing end of the chamber, with a passage being formed inside the chamber leading to the opening.

The end cap may internally also be provided with one or more formations adapted to guide the needle point to the mouth of the passage when the needle is displaced sideways within the end cap.

The tubular member may be made from a transparent material but could alternatively be made from an opaque coloured material.

The end cap is preferably made from a transparent material so that at least the point of the needle is visible.

The tubular member is preferably made from silicone rubber. It has been found that the tubular member can be made in a normal rubber injection moulding process using medical grade liquid silicone rubber. The silicone rubber preferably has a Shore hardness of approximately 30–80.

Less preferably the tubular member can be made from thermoplastic rubber or thin walled rubber.

The tubular member may be injection moulded or extruded, with an extrusion process being preferred because of its cost effectiveness.

The end cap is preferably made in a plastic injection moulding process using medical grade clear polystyrene. This ensures transparency compared for example to the use of polyethylene which results in a milky or cloudy product.

The passage in the end cap is preferably offset so that a wall of the passage and the blocking surface create a recessed formation which receives the needle point.

The passage is preferably flared and increases in cross sectional dimensions from its end inside the chamber to the opening at the blocking surface. This minimizes the likelihood that the point of the needle can become snagged on the wall of the passage and, in turn, reduces the likelihood that the point of the needle can thereby become damaged.

The silicone rubber used in the tubular member can withstand gamma or other radiation for sterilization purposes. The rubber is also stable up to a temperature of at least 200 deg.C and is ultraviolet resistant to a substantial extent.

The tubular member is preferably frictionally engaged with a hub of the needle at the first end and is frictionally engageable with the end cap at the second end. The end cap may include an external flange which assists in correctly locating the second end of the tubular member on the end cap.

The rim or flange also reinforces the chamber.

The end cap preferably has a relatively substantial axial dimension i.e. in the axial direction of the needle. Consequently when the tubular member is fully compressed a fairly substantial portion of the length of the needle is inside the tubular member. This acts as a safety feature for, if the needle does break while an injection is being given, it will in all probability break, not at the hub of the needle but inside the chamber. The needle will therefore be easier to extricate from a patient.

According to a still further feature of the invention the tubular member has internally between its ends areas of weakness which predispose the tubular member to bow laterally outwardly on axial compression. These areas of weakness may suitably be provided by notches in the edges of the slits.

The invention also extends to a combination of needle protective device and needle assembly, which comprises a needle assembly, including a hub and a needle projecting from the hub and the needle protective device of this invention engaged to the hub.

According to a preferred feature of the invention in which the axis of the needle is skewed relative to the longitudinal member of the tubular member to a position opposite the blocking position.

In one form of the invention the first end of the tubular member is normal to the longitudinal axis of the tubular member and is mounted on the needle hub skew to such normal.

In another embodiment of the invention, the first end of the tubular member is provided with a bevel and the tubular member is mounted on the needle hub with the bevel normal to the longitudinal axis of the needle hub.

BRIEF DESCRIPTION OF THE DRAWINGS

In the accompanying drawings which illustrate by way of example preferred embodiments of the invention:

FIG. 1 is a plan view of a needle protective device and needle assembly according to one embodiment of the invention, FIG. 2 is a longitudinal section of FIG. 1.

FIG. 8 is a plan view of the needle protective device and needle assembly according to FIG. 7 of the embodiment of the invention, and FIG. 9 is a longitudinal section of FIG. 8.

DETAILED DESCRIPTION OF THE DRAWINGS

Figure 3:
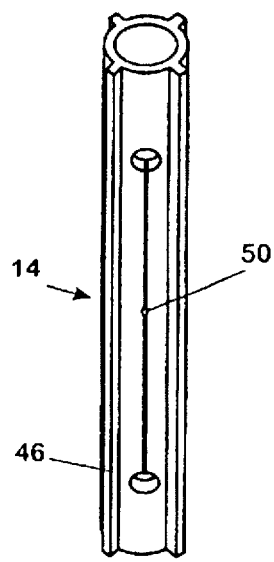
FIG. 3 is a perspective view of the tubular member of FIG. 1, FIGS. 4 and 5 are similar view of further embodiments of the tubular member.

FIGS. 1 and 2 of the accompanying drawings illustrate a needle protective device 10 according to the invention, and a needle assembly 12. The needle protective device includes a tubular member 14 and an end cap 16.

The tubular member 14 is made either from medical grade liquid or standard silicone rubber with a Shore hardness of 30 to 80 in an injection moulding or extrusion process. The silicone rubber is preferably transparent, but may be colour coded to indicate needle dimensions. Standard silicone rubber (i.e. in paste form) can be used for the extrusion process, whereas liquid silicone rubber can be used for both the extrusion and injection moulding process.

The tubular member 14 is in the form of a cylinder of substantially constant cross section having axially extending slits 18 therein. The slits 18 terminate at either end in round holes 20 to prevent the slits 18 from tearing.

The needle assembly 12 is conventional and includes a hub 22 with an end rim 24 and an elongate steel needle 26 extending from the hub.

The end cap 16 is injection moulded from medical grade clear polystyrene. As more clearly shown in FIG. 2 the end cap 16 defines an inner chamber 28, a sloping blocking surface 30 and a flared passage 32 extends to an opening 34 in the blocking surface 30. A flange 36 extends around an outer surface of the chamber 28. The flared passage 32 minimises the likelihood of the needle point snagging on the passage walls. Snagging can be even further minimised by providing a cut-away 37 in the wall of the passage 32. The inner wall of the chamber 28 is also formed with one or more guide ribs 38 which serve to guide the needle point into alignment with the mouth 40 of the flared passage 32, when the needle point is displaced sidewardly. The ribs 38 may also diverge rearwardly away from each other to facilitate guidance of the needle point.

The liquid silicone tubular member is frictionally engaged with the hub of the needle 26 and with the end cap, by stretching the ends of the tubular member 14 over the hub and end cap. It will be noted with reference to FIG. 2 that the end of the tubular member 14 is normal to it longitudinal axis and that the positioning of the end of the tubular member 14 on the needle hub 22 is skewed relative to the longitudinal axis of the hub 22, so that the needle will normally be disposed to lie adjacent the wall of the chamber 28 opposite to the location of the flared passage 32. The skewing is indicated by the gap 41 between the end of the tubular member 14 and the end rim 24 of the needle hub 22.

The sloping blocking surface 30 is provided to facilitate the administering of an intravenous injection where the needle is required to enter the patient at an angle.

For intravenous injection needles the tubular member 14 can be mounted on the needle hub 22 in such a way that the bevel on the needle point slopes in the same direction as the sloping blocking surface 30. Thus the operator simply by viewing the sloping blocking surface 30 will know that the bevel of the needle is in the correct disposition relative to the patients skin. It is not necessary to visually inspect the needle point itself to ensure this result.

The wall 42 of the passage 32 and the sloping blocking surface 30 define a safety chamber 44 for the point of the needle. It will be noted that the point of the needle is in alignment with the rear end of the wall 42 of the passage and thus by displacing the safety chamber 44 to one side, the needle can be aligned with the passage 32 for the injection procedure.

The tubular member 14 has a section of circumferentially disposed axial ribs 46 extend over it length. The ribs 46 enable the tubular member to be gripped at its ends when such ends are to be stretched over the needle hub and the end cap during assembly. These ribs 46 are particularly useful in an automated assembly process when they can be releasably engaged with suitable mechanical devices such as clamps to facilitate the required stretching of the tubular member. The ribs 46 also serve to stiffen the tubular member 14.

The ribs 46 can be moulded onto the tubular member 14 in an injection moulding process, but most conveniently can be formed in an extrusion moulding process which is the more cost effective of the two processes.

A tab 48 can be formed on the flange 36 to assist in orientation and location of the end cap 16 in the vibrating feed bowls used in an automated assembly process for fitting the tubular member onto the end cap and needle hub.

Finally it will be seen that along the edges of the axial slits 18 in the tubular member 14, notches 50 are provided. These notches 50 ensure that when the tubular member 14 is axially compressed it will be disposed to bow outwardly enabling the end cap 16 to be retracted until it encounters the needle hub 22.

Figure 4:
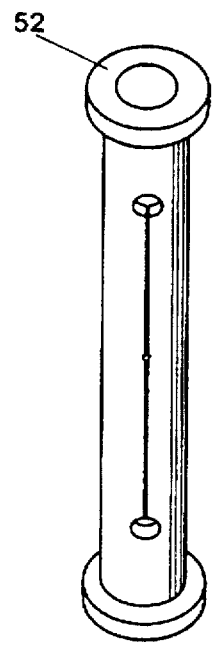
Figure 5:
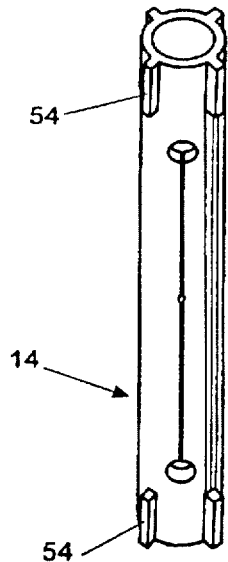
Figure 6:
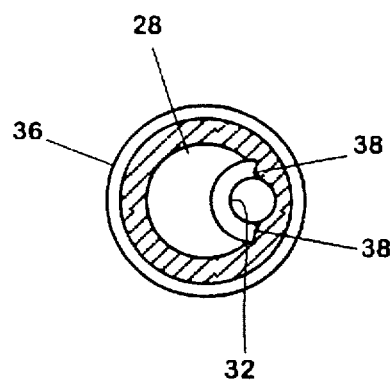
FIG. 6 is a section along the line 6—6 of FIG. 2.

FIG. 4 shows an injection moulded tubular member 14 with gripping means in the form of a radial flange 52 at either end. In FIG. 5 the ribs 46 on the tubular member 14 are replaced by lugs 54 adjacent either end of the tubular member 14.

It will be noted that the ribs 46 and the lugs 54 extend radially beyond the portion of the wall of the tubular member between adjacent ribs 46 and lugs 54. This stabilises the tubular member 14 against rolling in use or during the assembly process.

In use, the needle 26 being normally disposed in the position shown in FIG. 2 lies opposite the blocking surface 30 and therefore it is virtually impossible for the needle to inadvertently enter the flared passage 32. The needle 26 is constrained to such a disposition due to the resilience of the material from which the tubular member 14 is made in combination with the skewed relation of the tubular member 14 and the needle hub 22. When it is desired to extend the needle 26 through the passage 32, the safety chamber 44 is displaced sideways bringing the needle 26 in contact with one of the guide ribs 38 which automatically guides the needle point into alignment with flared passage 32.

In order to administer an injection, with the needle hub 22 fitted to the nozzle of a syringe, the needle is aligned with the passage 32 and the tubular member 14 is axially compressed to extend the needle through the passage 32. With the needle thus exposed the point of the needle is inserted into the patients skin and the tubular member 14 released to resile forward until the blocking surface 30 lies against the skin of the patient. At the end of the injection procedure as the needle is withdrawn from the patient the tubular member 14 axially expands causing the needle to be retracted through the passage 32 into the tubular member 14 with the needle point opposite the blocking surface 30.

Figure 7:
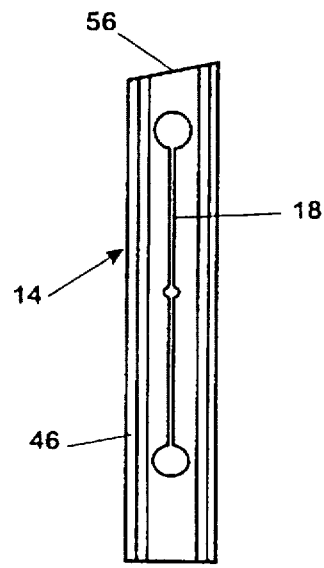
FIG. 7 is a side elevation of the tubular member of FIG. 3 of a second embodiment of the invention.

Referring to FIGS. 7, 8 and 9 there is shown an embodiment of the invention in which the tubular member 14 is provided with a bevel 56 at the end which is engageable with the hub 22. As will be noted the bevel end is flush against the end rim 24 of the needle hub 22 which has the effect of skewing the tubular member 14 on the needle hub 22 thereby resiliently biasing the needle 28 to a position opposite the blocking surface 30. It will be realised that a bevelled end may also be provided on the tubular member 14 in FIGS. 4 and 5 with a similar result.

It will be noted further with reference to FIG. 9 that the needle point 28 in this embodiment is disposed with the bevel on the needle point in an opposite direction to the bevel on the sloping blocking surface 30. This means that the point is distal from the outer wall of the passage 32, thus when the needle is protruded through the passage, snagging is virtually eliminated and the cut-out 37 can be dispensed with. The handling of the device during the handling procedure is greatly simplified. It will be noted that the bevel of the protruded needle is automatically in the correct position relative to the patients skin.

It should be realised that while the sloping blocking surface 30 is included in the illustrated embodiments because it facilitates insertion of the needle, this is not essential, and the end of the end cap may also be squared off.

I claim:

1. A needle protective device for a needle assembly having a needle hub and a needle projecting from the hub, the needle protective device comprising, a tubular member of resilient flexible material which extends about the needle, the tubular member having first and second ends, a first end of the tubular member having a bevel thereon and being mounted skew on and frictionally engaged with the needle hub with the bevel normal to the longitudinal axis of the needle hub, and an end cap mounted on the second end of the tubular member, the end cap having a blocking surface defining a hole through which the end of a needle may pass, the skew mounting biasing the tubular member to a position in which the end of the needle opposes the blocking surface.

2. The needle protective device of claim 1, in which the end cap defines a chamber which is open at one end, the end cap being attached at the one end to the second end of the tubular member, the blocking surface being disposed opposite the open end of the chamber; and a passage, provided in the chamber, leading to the hole in the blocking surface.

3. The needle protective device of claim 2, in which the end cap includes one or more formations adapted to guide the end of the needle towards a mouth of the passage when the end of the needle is displaced sideways towards the passage.

4. The needle protective device of claim 3, in which the passage flares outwardly from the hole towards the mouth.

5. The needle protective device of claim 2, in which the passage is offset to one side of the end cap.

6. The needle protective device of claim 1, in which the end of the needle is beveled and the blocking surface slopes in the same direction as the bevel.

7. The needle protective device of claim 1 in which a plurality of slits is provided in a wall of the tubular member, the slits extending in an axial direction between the first and second ends.

8. The needle protective device of claim 7, in which notches are formed in edges of the slits to predispose portions of the wall of the tubular member to bow outwardly when the first and second ends are urged together in the axial direction.

9. The needle protective device of claim 1, in which the end cap is of transparent material.

10. The needle protective device of claim 2, in which the passage is defined in part by a portion of an outer wall of the end cap, a cut out being provided in the outer wall portion and extending from a junction of the wall portion with the blocking surface.

11. The needle protective device of claim 1, in which an external flange is provided on the end cap.

12. The needle protective device of claim 11 including at least one gripping means on an exterior surface of the tubular member.

13. The needle protective device of claim 12 in which the gripping means includes a flange at or adjacent the first or second end of the tubular member.

14. The needle protective device of claim 12 in which the gripping means includes a plurality of lugs disposed about a circumference of the tubular member.

15. The needle protective device of claim 12 in which the gripping means includes one or more ribs extending along an outer surface of the tubular member.

16. The needle protective device of claim 12 in which a registration tab is provided on the end cap and protrudes laterally therefrom.

17. The needle protective device of claim 14 in which there are at least two ribs which protrude laterally beyond the portion of the wall of the tubular member between adjacent ribs.

18. The needle protective device of claim 15 in which the lugs protrude radially beyond the portion of the wall of the tubular member between adjacent lugs.

19. The combination of a needle protective device and a needle assembly: the needle assembly comprising a hub and a needle projecting from the hub, the needle protective device comprising a tubular member of resilient flexible material which extends about the needle, the tubular member having first and second ends a first end of the tubular member being mounted on and frictionally engaged with the needle hub, and an end cap having a blocking surface, the blocking surface defining a hole through which the end of a needle may pass, wherein the first end of the tubular member is mounted skew on the hub to bias the tubular member to a position in which the needle opposes the blocking surface.

20. The combination of claim 19 in which the first end of the tubular member has a bevel thereon and is mounted with the bevel normal to the longitudinal axis of the needle hub.

21. The combination of claim 20, in which the end cap defines a chamber which is open at one end, the end cap being attached at one end to the second end of the tubular member, the blocking surface being disposed opposite the open end of the chamber, and a passage, provided in the chamber, leading to the hole in the blocking surface.

22. The combination of claim 21, in which the end cap includes one or more formations adapted to guide the end of the needle towards a mouth of the passage when the end of the needle is displaced sideways towards the passage.

23. The combination of claim 22, in which the passage flares outwardly from the hole towards the mouth.

24. The combination of claim 21, in which the passage is off set to one side of the end cap.

25. The combination of claim 19 in which the end of the needle is bevelled, and the blocking surface slopes in the opposite direction to the bevel.

26. The combination of claim 19 in which a plurality of slits is provided in a wall of the tubular member, the slits extending in an axial direction between the first and second ends.

27. The combination of claim 26 in which notches are formed in the edges of the slits to predispose the wall portions of the tubular member to bow outwardly when the first and second ends are urged together in the axial direction.

28. The combination of claim 19 in which the end cap is of transparent material.

29. The combination of claim 20 in which the passage is defined in part by a portion of the outer wall of the end cap, and a cut out is provided in the outer wall portion and extending from a junction of the wall portion with the blocking surface.

30. The combination of claim 19 in which an external flange is provided on the end cap.

31. The combination of claim 19 including gripping means on an exterior surface of the tubular member.

32. The combination of claim 31 in which said gripping means includes a flange at or adjacent the first or second end of the tubular member.

33. The combination of claim 31 in which said gripping means includes a plurality of lugs disposed about the circumference of the tubular member.

34. The combination of claim 31 in which the gripping means includes one or more ribs extending along an outer surface of the tubular member.

35. The combination of claim 31 in which a registration tab is provided on the end cap and protrudes laterally therefrom.

36. The combination of claim 34 in which there are a plurality of ribs which protrude laterally beyond the portion of the wall of the tubular member between adjacent ribs.

37. The combination of claim 33 in the lugs protrude radially beyond the portion of the wall of the tubular member between adjacent lugs.

\* \* \* \* \*